(12) United States Patent
Chen

(10) Patent No.: US 7,125,685 B2
(45) Date of Patent: Oct. 24, 2006

(54) STABLE ISOTOPE, SITE-SPECIFIC MASS TAGGING FOR PROTEIN IDENTIFICATION

(75) Inventor: Xian Chen, Los Alamos, NM (US)

(73) Assignee: Los Alamos, National Security, LLC, Los Alamos, NM (US)

( * ) Notice: Subject to any disclaimer, the term of this patent is extended or adjusted under 35 U.S.C. 154(b) by 0 days.

(21) Appl. No.: 10/985,268

(22) Filed: Nov. 10, 2004

(65) Prior Publication Data

US 2005/0124014 A1    Jun. 9, 2005

Related U.S. Application Data

(63) Continuation of application No. 10/043,965, filed on Jan. 11, 2002, now abandoned.

(60) Provisional application No. 60/261,716, filed on Jan. 12, 2001.

(51) Int. Cl.
*C12Q 1/37* (2006.01)

(52) U.S. Cl. .................. 435/23; 435/24; 435/68.1

(58) Field of Classification Search .......... 435/23, 435/24, 68.1
See application file for complete search history.

(56) References Cited

U.S. PATENT DOCUMENTS

| | | | |
|---|---|---|---|
| 6,653,076 B1* | 11/2003 | Franza et al. ............ | 435/6 |
| 2002/0076817 A1* | 6/2002 | Figeys et al. ............ | 436/6 |
| 2003/0044864 A1* | 3/2003 | Short et al. ............. | 435/7.23 |
| 2004/0072251 A1* | 4/2004 | Anderson ................ | 435/7.1 |
| 2005/0164326 A1* | 7/2005 | Figeys et al. ............ | 435/23 |

OTHER PUBLICATIONS

Waugh D. et al. Genetic Tools for Selective Labeling of Proteins with Alpha 15 N Amino Acids. J of Biomolecular NMR. vol. 8, pp. 184-192, 1996.*
Veenstra T. et al. Proteome Analysis Using Selective Incorporation of Isotopically Labeled Amino Acids. J American Soc for Mass Spec. Elsevier Science Inc. 11(1)78-82, 2000.*

* cited by examiner

*Primary Examiner*—Ralph Gitomer
(74) *Attorney, Agent, or Firm*—Bruce H. Cottrell; Robert P. Santandrea

(57) ABSTRACT

Proteolytic peptide mass mapping as measured by mass spectrometry provides an important method for the identification of proteins, which are usually identified by matching the measured and calculated m/z values of the proteolytic peptides. A unique identification is, however, heavily dependent upon the mass accuracy and sequence coverage of the fragment ions generated by peptide ionization. The present invention describes a method for increasing the specificity, accuracy and efficiency of the assignments of particular proteolytic peptides and consequent protein identification, by the incorporation of selected amino acid residue(s) enriched with stable isotope(s) into the protein sequence without the need for ultrahigh instrumental accuracy. Selected amino acid(s) are labeled with $^{13}C/^{15}N/^{2}H$ and incorporated into proteins in a sequence-specific manner during cell culturing. Each of these labeled amino acids carries a defined mass change encoded in its monoisotopic distribution pattern. Through their characteristic patterns, the peptides with mass tag(s) can then be readily distinguished from other peptides in mass spectra. The present method of identifying unique proteins can also be extended to protein complexes and will significantly increase data search specificity, efficiency and accuracy for protein identifications.

30 Claims, 9 Drawing Sheets

STABLE ISOTOPE, SITE-SPECIFIC MASS TAGGING FOR PROTEIN IDENTIFICATION

RELATED APPLICATIONS

This application is a continuation of application Ser. No. 10/043,965, filed on Jan. 11, 2002., and now abandoned, which claims the benefit of provisional application 60/261,716 filed Jan. 12, 2001.

STATEMENT REGARDING FEDERAL RIGHTS

This invention was made with government support under Contract No. W-7405-ENG-36 awarded by the U.S. Department of Energy to The Regents of The University of California. The government has certain rights in the invention.

FIELD OF THE INVENTION

The present invention relates generally to protein identification using mass spectrometry and, more specifically, to the stable isotope mass tagging of selected amino acids which are incorporated into proteins in a sequence-specific manner during cell culturing to enable protein identification from the characteristic patterns in the mass spectra of proteolytic peptides.

BACKGROUND OF THE INVENTION

Proteomics is a newly emerging field in the post-genomics era[1]. A major activity of proteomics is the identification of unique proteins in cellular complexes in a high throughput mode[2]. Peptide mass mapping followed by database searching is a major approach towards the identification of a protein using mass spectrometry (MS). Using this approach the measured and calculated masses of proteolytic peptides are compared for a best mass-fit to possible proteins[3,4]. The most commonly used method is an in-gel digestion of the protein spots separated by two dimensional polyacrylamide gel electrophoresis (2D PAGE) for analysis by matrix-assisted laser desorption/ionization time-of-flight (MALDI-TOF) MS[5,6]. Mass accuracy and precision are of prime importance to ensure specificity of the search for a target protein in database searches.

The mass-to-charge (m/z) ratios of a large number of proteolytic peptides covering much of the protein sequence must be precisely determined. Too few proteolytic peptides from a target protein in a MALDI-TOF MS spectrum reduces the specificity and precision of the database search and can give false positives. Currently, the typical sequence coverage of a protein in a MALDI-TOF MS spectrum is less than 40%[7-14]. This depends largely on sample availability[7], sample preparation methods[8], matrix solution conditions[9], and matrix crystal morphology[10], as well as the physical properties of proteins such as charged side chains[11,12], peptide hydrophobicity[13], and the potential to form stable secondary structures[14]. In most cases, MS data acquisition and interpretation have proven to be time-consuming in the identification of unique proteins in complexes because of problems such as low sample availability, background or artifact ions, mass degeneracy of peptides from protein impurities and post-synthetic modifications of proteins as examples[15] Ultrahigh mass accuracy provided by high-cost instruments is often required to determine the absolute m/z values of these proteolytic fragments[16,17]. To increase the specificity of identification of proteolytic peptides, the external labeling of the C-termini of tryptic peptides with $H_2O$ containing 50% $^{18}O$ during trypsin digestion has been used[18,19]. Although this is a useful method for excluding unrelated peaks from the data search, its selectivity and sensitivity is poor because only the C-termini of all tryptic peptides are labeled with $^{18}O$.

It is necessary to extend the limited resource of peptide signals available in MALDI-TOF MS spectra for characterizing proteins by further increasing the specificity of proteolytic peptide identification. Stable isotope labeling; that is, the replacement of $^{13}C$ for $^{12}C$, $^{15}N$ for $^{14}N$, or $^2H$ for $^1H$, in proteins or DNA oligomers can generate internal mass "signatures" with characteristic mass shifts in their isotopic distribution patterns without affecting their chemical and structural properties[20]. Uniformly $^{15}N$-labeled proteins have been generated for the accurate MS-based quantitation of protein expression[21] and for improvements in the sensitivity and accuracy of molecular mass measurements[22].

Stable isotope $^{13}C/^{15}N$-labeled nucleotides have successfully been incorporated as internal markers to determine the nucleotide composition of PCR products[23].

Accordingly, it is an object of the present invention to increase the specificity of mass spectrometric proteolytic peptide identification.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for identifying a protein hereof includes the steps of: separating the protein from other proteins; digesting the protein, thereby forming first proteolytic peptides; acquiring the monoisotopic mass distribution spectrum of the first proteolic peptides and acquiring the m/z values therefor; incorporating an amino acid 100% labeled with a stable isotope into the protein in a sequence-specific manner; separating the protein bearing the labeled amino acid from other proteins; digesting the protein bearing the labeled amino acid, thereby forming second proteolytic peptides; acquiring the monoisotopic mass distribution spectrum of the second proteolytic peptides and acquiring the m/z values therefor; comparing the monoisotopic mass distribution spectrum of the second proteolytic peptides with the monoisotopic mass distribution spectrum of the first proteolytic peptides to determine the amino acid composition of the first proteolytic peptides and the second proteolytic peptides, whereby the protein is identified from the m/z values of the first proteolytic peptides and the m/z values of the second proteolytic peptides and the amino acid composition of the first proteolytic peptides and the second proteolytic peptides. The order in which the mass analysis of the labeled proteolytic peptides or the mass analysis of the unlabeled proteolytic peptides is performed is not important.

Preferably, the step of incorporating the 100% labeled amino acid into the protein in a sequence-specific manner further includes the steps of: introducing the 100% labeled amino acid into a cell capable of expressing the protein; and inducing the cell to express the protein.

In another aspect of the present invention, in accordance with its objects and purposes, the method for identifying a protein hereof includes the steps of: incorporating an amino acid 100% labeled with a stable isotope into the protein in a sequence-specific manner at a variable number of the sites for that amino acid in the protein, forming thereby a mixture of partially labeled proteins; separating the mixture of partially labeled proteins from other proteins; digesting the mixture of partially labeled proteins, thereby forming proteolytic peptides; and acquiring the monoisotopic mass distribution spectrum of the proteolytic peptides and acquiring the m/z values therefor, whereby the protein is identified from the m/z values of the proteolytic peptides and the amino acid composition of the proteolytic peptides.

Preferably, the step of incorporating the 100% labeled amino acid into the protein in a sequence-specific manner at a variable number of sites for that one amino acid in the protein, further includes the steps of: introducing the 100% labeled amino acid and a chosen amount of an unlabeled same amino acid into a cell capable of expressing the protein; and inducing the cell to express the protein.

Benefits and advantages of the present incorporation of mass labels into specific proteolytic fragments significantly increase datasearch specificity, efficiency and accuracy for peptide sequencing and protein identification.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 3a shows the PSD fragment ion mass spectra of the fragment of $^{64}$FLFEGQ$^{70}$R containing unlabeled glycine residue, while

FIG. 4a shows delayed-extraction MALDI mass spectra of tryptic digests of 50% Gly-$d_2$ labeled E. coli cell lysate, while

DETAILED DESCRIPTION

Figure 1:
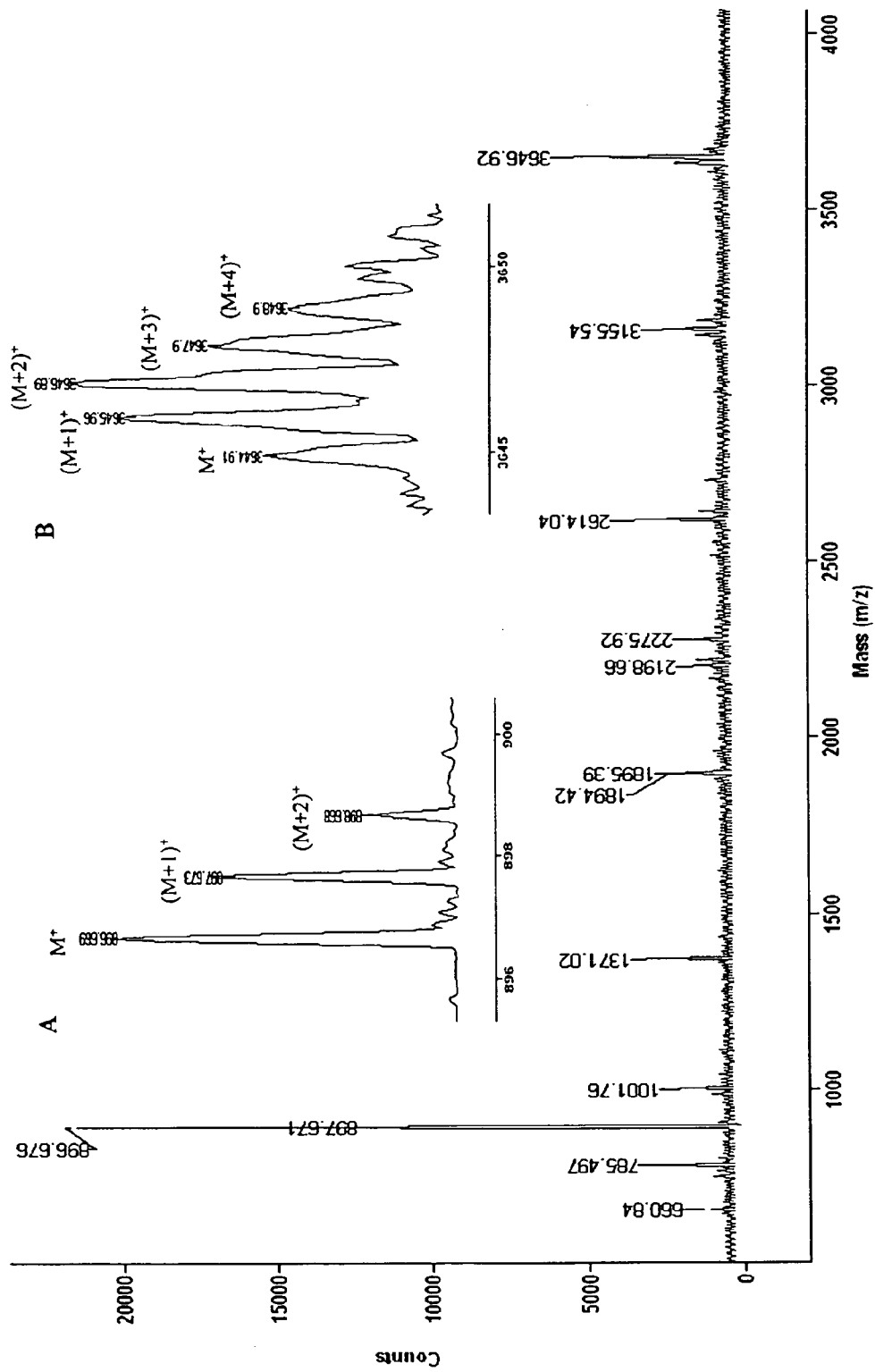
FIG. 1 shows delayed-extraction MALDI mass spectra of tryptic digests of the unlabeled UBL1.

Briefly, the present invention includes the incorporation of stable isotope-labeled amino acid residue(s) in proteins to "mass-tag" some proteolytic peptides according to their content of these labeled residue(s). Stable isotope labeling of proteins are specific for particular amino acid residues[24-26]. Particular labeled amino acid are incorporated into proteins during cell growth or in an in vitro transcription/translation system[26] in a manner that provides residue-specific mass-labeled proteins without scrambling of the label to other types of residues[24]. A comparison of the masses of the peptides generated from proteolytic digestion of the residue-specific labeled protein with those of an unlabeled control assists in identifying the mass-tagged peptides, because modern mass spectrometry, including MALDI-TOF MS, permits the accurate determination of these changes with monoisotopic resolution[27,28]. This provides an additional constraint of the amino acid identity of mass tagged peptides to enable accurate peptide identification. Furthermore, the magnitude of the mass shifts for peptides reflect the content of particular amino acid residue(s). A smaller number of identified mass-tagged peptides is then used for more effective protein identification. It should be mentioned that other mass spectrometers, such as electrospray mass spectrometers, can effectively be employed in accordance with the teachings of the present invention.

Although partial amino acid sequences of selected peptides can be obtained by postsource decay (PSD) experiments[29,30], many precursor ions obtained by delayed-extraction (DE) MALDI do not produce sufficient PSD fragmentation to allow the identification of even short sequence tags[30]. In accordance with the teachings of the present invention, the characteristic monoisotopic distribution pattern(s) of labeled amino acid residues provide internal marker(s) for the assignment of PSD derived peptides. Thus, the incorporation of mass labels into specific proteolytic fragments significantly increase datasearch specificity, efficiency and accuracy for peptide sequencing and protein identification.

Having generally described the present invention, the following detailed description additional information.

I. Materials and Procedures:

A. Chemicals: Stable isotope enriched amino acid precursors, L-Methionine-99.9%-$d_3$ (Met-$d_3$) and Glycine-99.9%-2,2-$d_2$ (Gly-$d_2$) were purchased from Isotec INC. (Miamisburg, Ohio).

B. E. coli Strains for Residue-Specific Labeling of Proteins: 21 strains of bacteria, each containing a different genetic defect closely linked to a selectable transposon marker were used to construct strains of E. coli with effective genotypes for residue-specific, selective labeling of proteins with almost any stable isotope-labeled amino acid. By using strains which have been modified to contain the appropriate genetic lesions to control amino acid biosynthesis, dilution of the isotope label by endogenous amino acid biosynthesis and scrambling of the label to other types of residues was avoided. Clearly other cell lines can be generated to perform the same task.

1. E. coli strain CT2 was constructed by transduction of the BL21 (DE3) strain to tetR with a P1 lysate from MF14, and then screening for the gly-phenotype[26]. This derivative of BL21(DE3) was used for the selective labeling of proteins with the stable isotope-labeled glycine.

2. Similarly, CT13 was constructed by transducing BL21 (DE3) to tetR with a P1 lysate from MF 21, and then screening for the met-phenotype (metA-). This metA- derivative of BL21(DE3) has the ideal genotype for selective isotope labeling with methionine.

C. Residue-Specific Labeling of Proteins and Purification. The expression plasmid of UBL1 was transformed into both CT2 BL21(DE3) and CT13 BL21(DE3). According to the protocol given by Muchmore et al.[27], the CT2 BL21(DE3) cells were grown in M9 minimum media supplemented with 0.2 g per liter of the L-Methionine-99.9%-$d_3$, 0.02 g per liter of unlabeled cysteine, and 0.2 g per liter of each of other unlabeled amino acids. The CT13 BL21(DE3) cells were fed with a similar mixture that contained the labeled precursor, 0.2 g of Glycine-99.9%-2,2-$d_2$. These cells were induced with 1 mM isopropylthiogalactoside (IPTG) for protein expression. It is clear that other amino acids than Methionine and Glycine can be labeled and used in accordance with the teachings of the present invention. Moreover, other inducing agents than IPTG can be employed. The corresponding unlabeled protein was expressed in regular LB media. The His-tagged proteins were purified in a buffer of 150 mM ammonium acetate (NH$_4$OAC), pH 7.0 with a gradient of 0–150 mM imidazole.

D. Tryptic Digestion and MALDI-MS Analysis. The protein samples were further desalted using C18 ZipTips (Millipore) and eluted with aqueous 50% acetonitrile containing 0.1% TFA. After lyophilizing, the samples were resuspended in a buffer of 25 mM ammonium bicarbonate (NH$_4$HCO$_3$), pH 8.0. The unlabeled protein was mixed with Met-$d_3$- or Gly-$d_2$-labeled proteins in a variety of molar ratios. Trypsin (Boehringer Mannheim) was added in the final concentration of 10 μg/ml and the mixture was incubated for 1 h or 16 h at 37° C. respectively. For mass spectrometry analysis, 1 μl of sample was mixed with 1 μl of a matrix solution (10 mg/ml) of α-cyano-4-hydroxycinnamic acid which was prepared by dissolving 10 mg in 1 ml of aqueous 50% acetonitrile containing 0.1% trifluoroacetic acid (TFA).

Mass spectrometry experiments were carried out on a PE Voyager DE-STR Biospectrometry workstation equipped with a N$_2$ laser (337 nm, 3-ns pulse width, and 20-Hz repetition rate) in both linear and reflectron mode (PE Biosystems, Framingham, Mass.). The mass spectra of the tryptic digests were acquired in the reflectron mode with delayed extraction (DE). The m/z values of proteolytic peptides were calibrated with Calimix 2 including Angiotensin I at 1297.51 Da (M$^+$) and Insulin at 5734.59 Da (M$^+$).

E. Mass Tagging in an *E. coli* Strain and the Target Protein Identification.

The *E. coli* BL21 (DE3) cell strain containing the UBL1 expression vector was cultured in M9 media supplemented with a mixture of amino acids including 50% labeled amino acid precursors (Gly-$d_2$ or Met-$d_3$) respectively. The cells were then induced with 1 mM IPTG. An aliquot of the cell culture was collected 30 min. after the IPTG induction when the target protein did not overwhelm the proteins in the total cell extract. After centrifugation of the cell aliquot, the resulting pellet was resuspended and sonicated in a buffer of 1 mM DTT and 20 mM NH$_4$HCO$_3$ at pH 8.0. The supernatant of the cell extract was treated with trypsin (10 μg/ml) overnight without purification. The cell extract containing the tryptic digests was then desalted by C18 ZipTip (Millipore) and analyzed using MALDI-TOF MS.

F. Mass Tagging for a Complex Mixture and MALDI-MS Analysis. *E. coli* BL21(DE3) cell strains containing the UBL1 and UBC9 expression vectors were mixed in the same copy numbers and grown in M9 media supplemented with a mixture of amino acids that included 50% deuterium-labeled glycine (Gly-$d_2$). Both UBC9 and UBL1 were readily expressed and labeled with Gly-$d_2$ at all glycine residues in the *E. coli* strains upon IPTG induction. The cell pellet was resuspended, sonicated and lysed in a buffer of 1 mM DTT and 20 mM NH$_4$HCO$_3$ at pH=8.0. The Pharmacia Biotech FPLC with a gel filtration mini-column (Superdex 75, 1.0 cm×10 cm, Pharmacia Biotech) was used to isolate the complex of UBL1 and UBC9 from the cell lysate. The same buffer of 1 mM DTT and 20 mM NH$_4$HCO$_3$ at pH=8.0 was used for the protein elution. The fraction containing the complex was lyophilized and then treated with trypsin (10 μg/ml in 10 mM NH$_4$HCO$_3$, pH 8) overnight.

G. Post-Source Decay (PSD) Measurements[29,30]. PSD fragment ion spectra were acquired for those peptides containing the labeled amino acids after isolation of the appropriate precursor ion. Fragment ions were refocused onto the final detector by stepping the voltage applied to the reflectron in the following ratios: 1.0000 (precursor ion segment), 0.9126, 0.8000, 0.7000, 0.6049, 0.4125, 0.2738, 0.1975, 0.1213, and 0.0900.

II. Results:

A. Identification of the Tryptic Fragments Containing Stable Isotope-labeled Amino Acids.

The TABLE lists the theoretical m/z values and sequences of peptides generated by tryptic digestion of the ubiquitin-like protein, UBL1[31]. Partially $^2$H(d)-labeled glycine and methionine residues, which are widely distributed in the protein, were incorporated as the labeled precursors for mass signatures of certain peptides in the protein. Two residue-specific labeled versions of UBL1, designated UBL1-Met-$d_3$, and UBL1-Gly-$d_2$ were generated. The protein, UBL1-Met-$d_3$, was extracted from *E. coli* strain BL21(DE3) CT13 cells transformed with the UBL expression vector and had the $^2$H-labeled precursor, methionine-99.9%-S-methyl-$d_3$ (Met-$d_3$), incorporated at all of the methionine sites of the protein. Similarly, the glycine-specific labeled protein, UBL1-Gly-$d_2$, extracted from *E. coli* BL21(DE3) CT2 cells, had the $^2$H-labeled precursor, glycine-99.9%-2,2-methene-$d_2$ (Gly-$d_2$), incorporated at all glycine sites. Thus, for peptides containing Met-$d_3$ or Gly-$d_2$ there was a 3 or 2 Da mass increase per methionine or glycine residue, respectively, relative to their unlabeled counterparts.

Reference will now be made in detail to the present preferred embodiments of the invention which are illustrated in the accompanying drawings. FIG. 1 shows the mass spectrum obtained from a tryptic digest of the unlabeled UBL1. The PE Voyager-DE STR MALDI-TOF MS has a mass resolution, M/ΔM, of 5000 which is sufficient to resolve monoisotopic peaks of all the tryptic peptides of masses up to 5000 daltons (Da). Inset A shows an expanded view of the monoisotopic distribution pattern corresponding to the relative abundance of isotopes, M$^+$:(M+1)$^+$:(M+2)$^+$ . . . (M refers to the mass corresponding to the most abundant isotope) of a small tryptic peptide with a m/z value of 896.67 Da (M$^+$ ion). As the number of atoms increases, the less abundant isotopes such as $^{13}$C, $^{15}$N or $^2$H also increase, so that at a higher m/z the isotopic pattern is more pronounced as shown in inset B (the m/z of M$^+$ ion is at 3644.91 Da). Ion fragments having m/z values of 1895.39, 2198.66, 2275.92, 2614.04 and 3155.54 probably derive from incomplete digestion and impurities were not assigned to the protein.

Figure 2A:
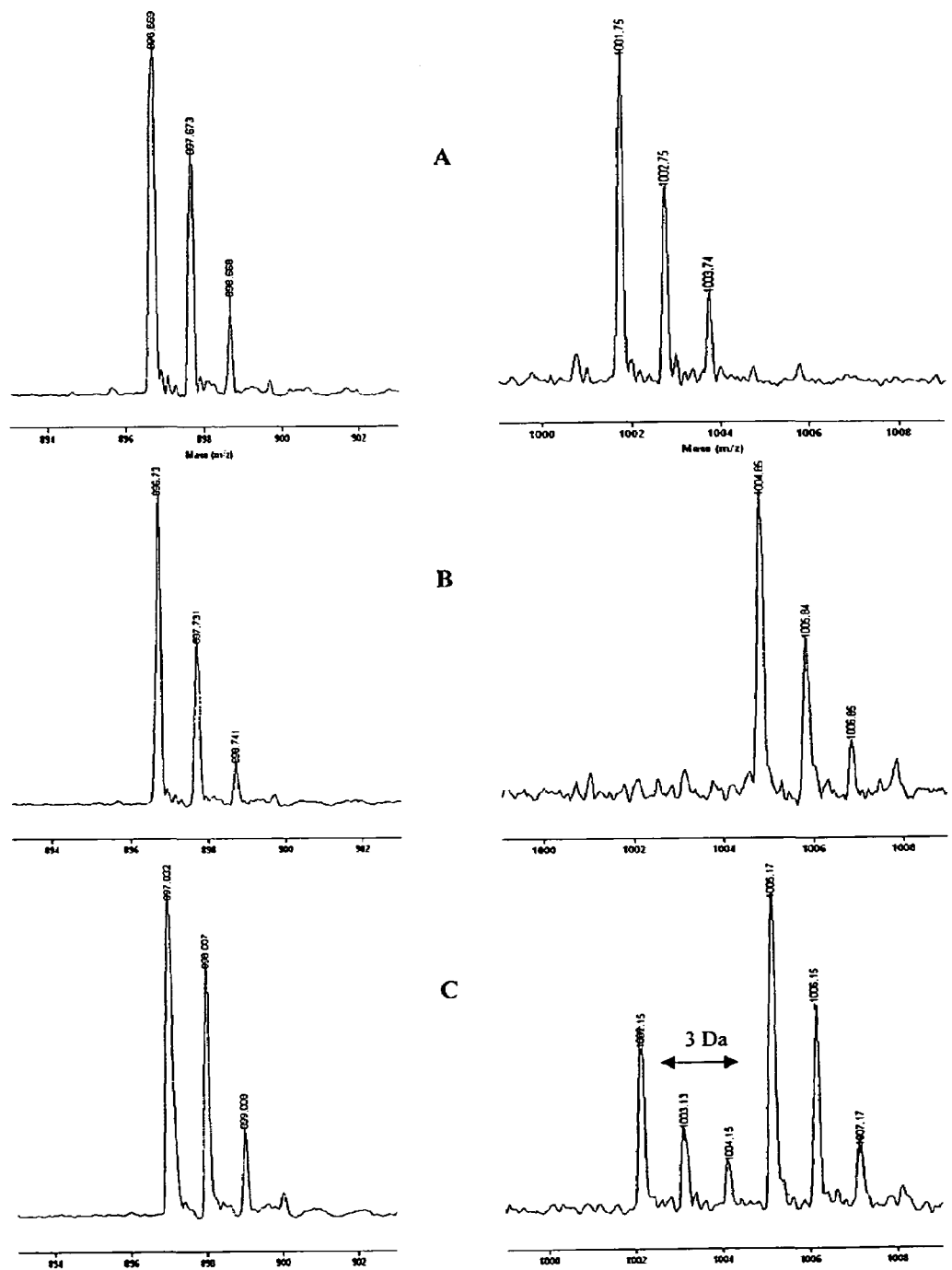
FIG. 2a shows monoisotopic patterns of peptides at m/z of 896.67 Da ($M^+$) and 1001.75 Da ($M^+$) from tryptic digestion of (A) unlabeled UBL1; (B) Met-$d_3$ labeled UBL1; and (C) a mixture of the Met-$d_3$ labeled and unlabeled UBL1.

For a given monoisotopic distribution pattern of the peptides, particular fragment ions containing the labeled precursor(s) shift in mass with respect to the unlabeled control. FIG. 2a shows the MALDI-TOF mass spectra of two proteolytic peptides from: (A) unlabeled UBL1; (B) UBL1-Met-$d_3$; and (C) a mixture of (A) and (B) in a 1:2 ratio. It was observed that the monoisotopic M$^+$ ion at 1004.85 Da from UBL1-Met-$d_3$ (B) was 3 Da heavier than that of the unlabeled UBL1 (1001.75 Da) (A) because of the presence of the labeled methionine (FIG. 2a(A)). By contrast, no peak shift was detected for the M$^+$ ion at 896.67 Da also from the Met-d$_3$ labeled protein (FIG. 2a(B)). For (C), a pair of monoisotopic peaks separated by 3 Da between M$^+$ ions of 1002.15 Da and 1005.17 Da was observed (FIG. 2a(C), right trace) but not at 896.67 Da (FIG. 2a(C), left trace). The ratio of the intensities of the upper and lower M$^+$ mass ions; that is, the ratio of the labeled and unlabeled proteins is approximately 2:1. Because the mass tag of a labeled methionine residue (Met-d$_3$) is 3 Da, there is one Met residue in the peptide at 1001.75 Da (M$^+$ ion) and none in the peptide at 896.67 Da (M$^+$ ion). Thus, the 3-Da mass split pattern is characteristic for Met-d$_3$-tagged peptides of the protein. It may also be noted that the monoisotopic distribution patterns of these labeled peptides are essentially unchanged when compared to the unlabeled peptides. This is because only a few protons are replaced by deuterium in the labeled precursors.

Figure 2B:
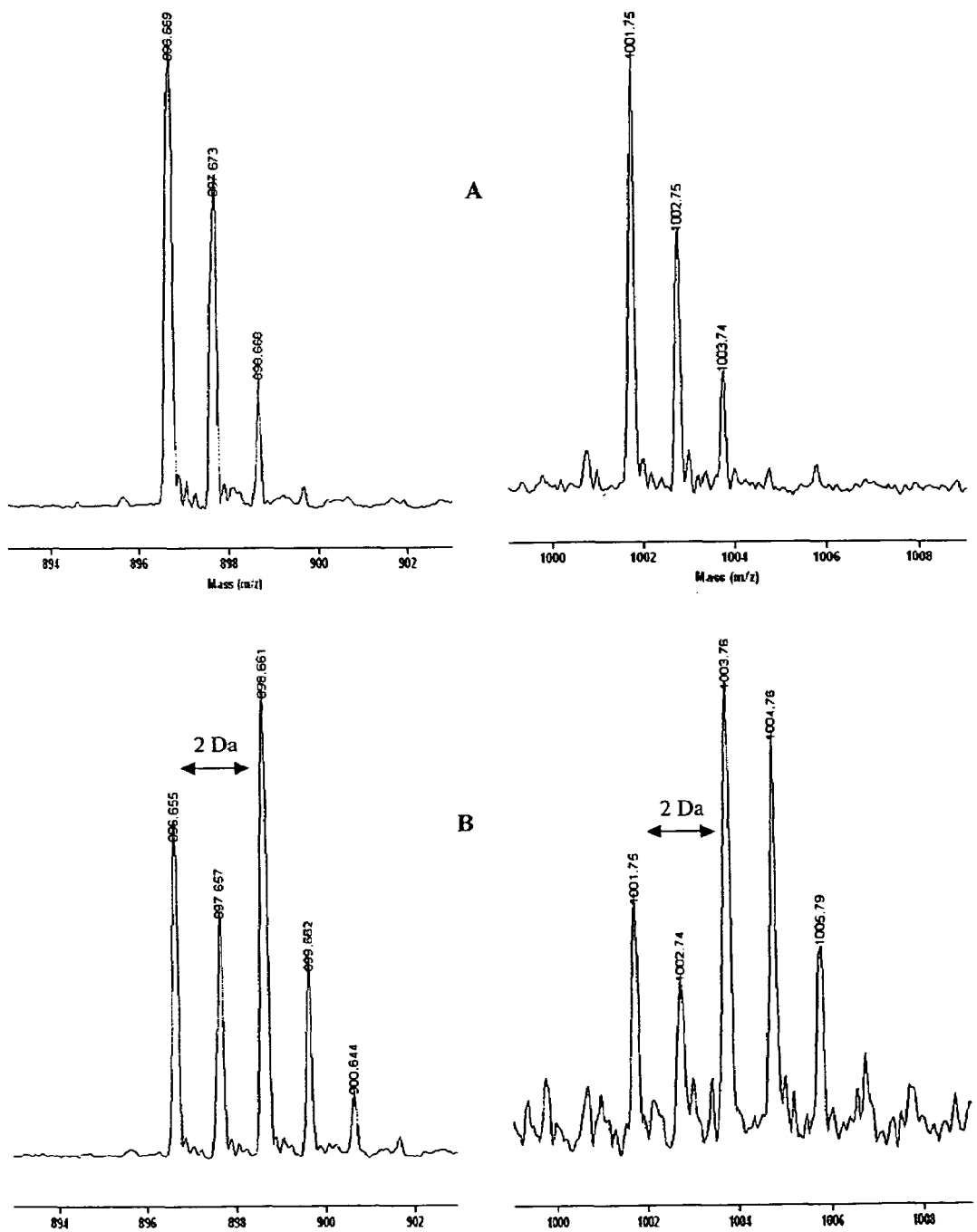
FIG. 2b shows monoisotopic patterns of peptides at m/z of 896.67 Da ($M^+$) and 1001.75 Da ($M^+$) from tryptic digestion of: (A) unlabeled UBL1; and (B) a mixture of Gly-$d_2$ labeled and unlabeled UBL1.

FIG. 2b shows monoisotopic patterns of peptides at m/z of 896.67 Da (M$^+$) and 1001.75 Da (M$^+$) from tryptic digestion of: (A) unlabeled UBL1; and (B) a mixture of the Gly-d$_2$ labeled and unlabeled UBL1 (2:1 molar ratio). The incorporation of a Gly-d$_2$ label can be recognized by the 2-Da split between the monoisotopic peaks of the unlabeled and labeled peptides. A pair of monoisotopic peaks separated by 2 Da with an intensity ratio of approximately 2:1 (upper to lower mass components) was observed in the m/z ranges of 896.67–898.66 and 1001.75–1003.76, for approximately 60% Gly-labeled UBL (UBL1-gly-d$_2$). This corresponds to one Gly residue in each of the peptides (FIG. 2b(B)). In this case, the fragment ion of 896.67 Da (M$^+$ ion) has one Gly and no Met, and the tryptic fragment of 1001.75 Da (M$^+$ ion) contains both a Gly and a Met residue. The characteristic mass-split pattern (with 2 or 3 Da spacing) for the immediate recognition of mass-tagged peptides of UBL1 containing the labeled precursor(s) is thus established. In comparison with the theoretically calculated m/z values listed in the TABLE, these two fragments were identified as $^{64}$FLFEGQ$^{70}$R and $^{55}$QGVPMNSL$^{63}$R, respectively. Although the fragment of $^{71}$IADNHTPK has a similar m/z value of 895.46 Da for the fragment 64-70, no mass tag or split was observed for this fragment in either mixture. The presence or absence of internal mass tags therefore can readily distinguish between these two peptides.

Figure 2C:
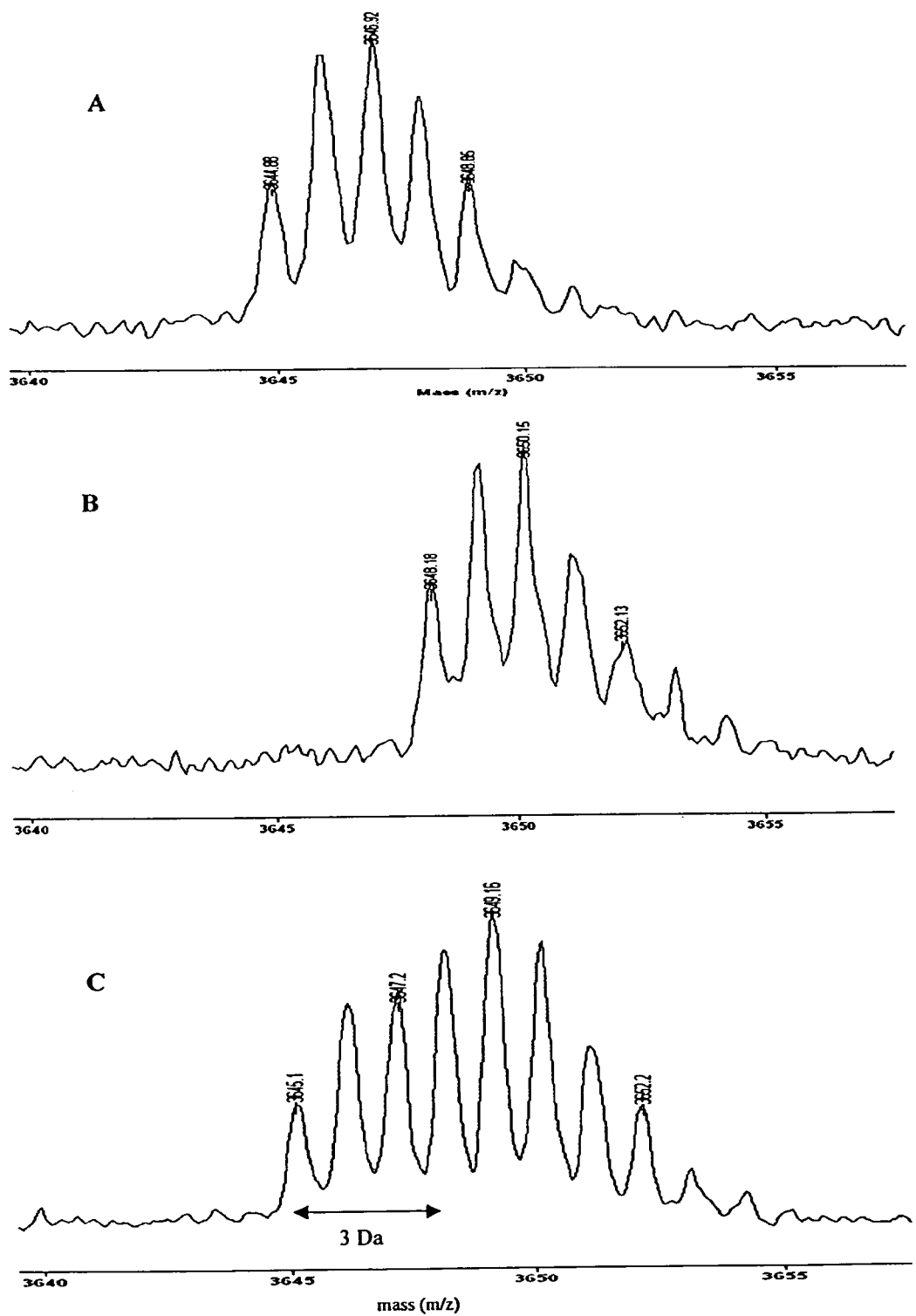
FIG. 2c shows the characteristic isotopic patterns of the large tryptic digest at m/z of 3644.88 ($M^+$) for: (A) unlabeled UBL1; (B) Met-$d_3$ labeled UBL1; and (C) a mixture of the Met-$d_3$ labeled and unlabeled UBL1.

FIG. 2c shows the characteristic isotopic patterns of the large tryptic digest at m/z of 3644.88 (M$^+$) for: (A) unlabeled UBL1; (B) Met-d$_3$ labeled UBL1; and (C) a mixture of the Met-d$_3$ labeled and unlabeled UBL1 (2:1 molar ratio). The incorporation of a Met-d$_3$ label can be recognized by the 3-Da split between the monoisotopic peaks of the unlabeled and labeled peptides. Changes in isotopic distribution patterns (FIG. 2c) were also observed for the larger fragment ions of 3644.88 Da (M$^+$ ion) and 4521.65 Da (M$^+$ ion) (incomplete digestion product, data not shown). For large fragments, the number of monoisotopic peaks increase in proportion to the number of atoms. A mass shift of 3 Da with respect to their unlabeled control was observed for both fragment ions in the digestion product of UBL1-Met-d$_3$ (Compare FIGS. 2c(A) and 2c(B) for the 3644.88. Da fragment ion). FIG. 2c(C) shows the mass spectrum of a mixture of the unlabeled and Met-d$_3$ labeled peptide of 3644.88 Da. Similarly, a mass shift of 6 Da was observed (data not shown) for both peptides of m/z values of 3645.10 Da and 4521.99 Da for Gly-labeled UBL1 (UBL1-Gly-d$_2$) which implies three Gly-d$_2$ in both peptides. The peak set at 4521.99 Da (M$^+$ ion) was observed to diminish with longer digestion times (overnight at 37° C.). This is consistent with a peptide resulting from an incomplete digestion product. The difference in mass between these two peaks (3645.10 and 4521.99 Da) is 876.89 Da which is close to the m/z value of the fragment $^{71}$IADNHTPK (M$^+$=895.46) minus the mass of a water (H$_2$O) molecule. Because the M$^+$ fragment ion at 4521.99 Da displays the same mass tag and isotopic distribution pattern as the fragment ion at 3645.10 Da, it is clear that both peptides contain one Met residue and three Gly residues and share a common segment. Thus, the fragment of 4521.99 Da is from the incomplete digestion of the last two fragments at the C-terminal of the protein; that is, $^{71}$IADNHTP$^{78}$K and $^{79}$ELGMEEEDVIEVYQEQTGGHSTVLEHHHHH$^{107}$H (bold type indicates the labeled Gly, while the labeled Met is underlined). The hydrolysis of the fragment of 71-107 results from the addition of a water molecule at C-terminal of the fragment of 71-78 to form the fragments 71–78 (the M$^+$ ion at 895.46 Da) and 79-107 (the M$^+$ ion at 3645.10 Da). It also suggests that the tryptic site of $^{78}$Lys linking the two peptides of the 71-78 and 79-107 is probably located in the core of the protein and partially shielded from tryptic digestion. This observation is consistent with the results of NMR studies of UBL1 indicating that $^{78}$Lys is included in an α-helical segment[32]. This is an example of the use of mass tags to indicate possible secondary structure of a protein.

B. Internal Isotopic Markers for Highly Selective Peptide Sequencing Using Post-source Decay (PSD)[29,30].

Figure 3A:
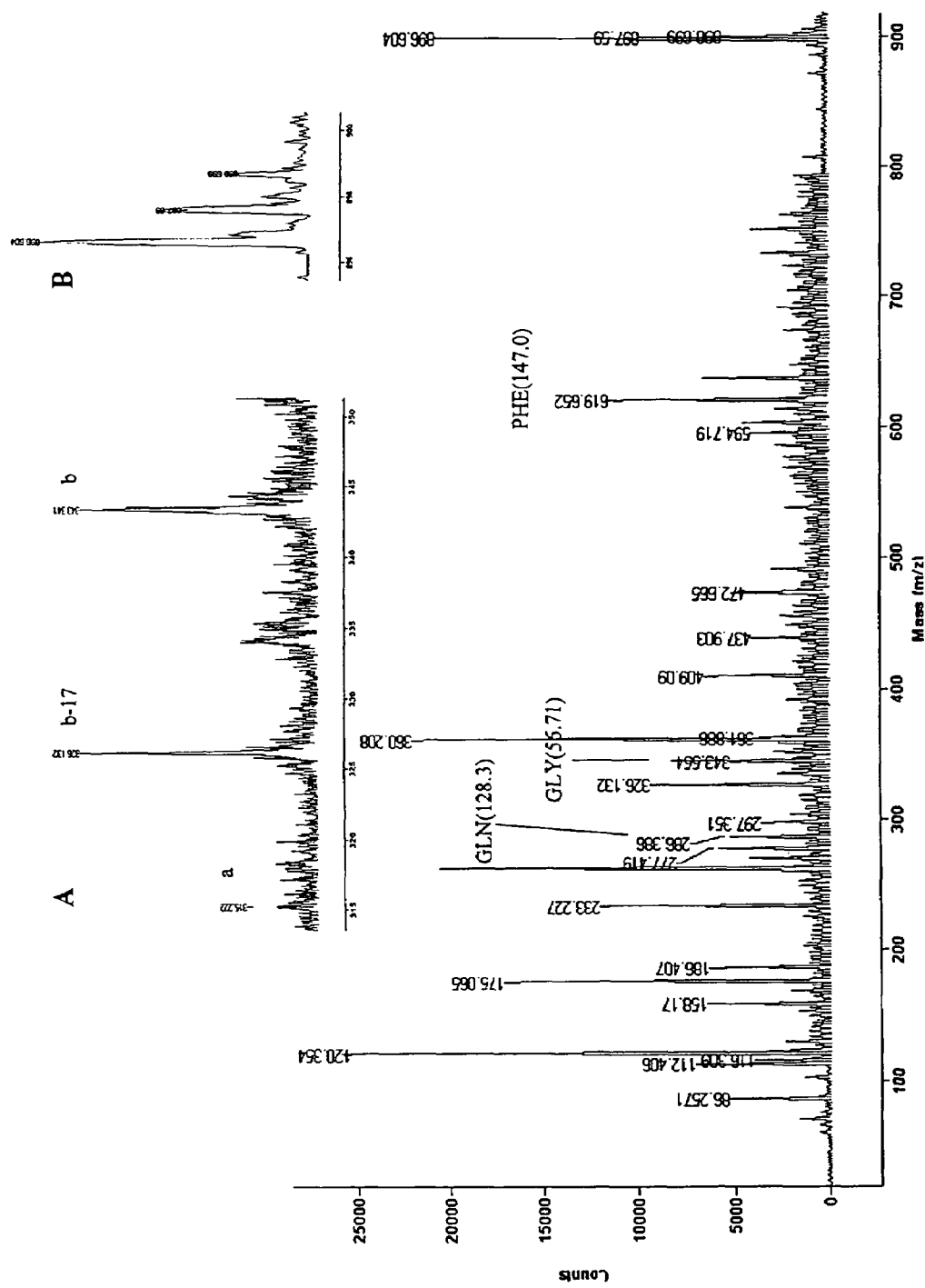
Figure 3B:
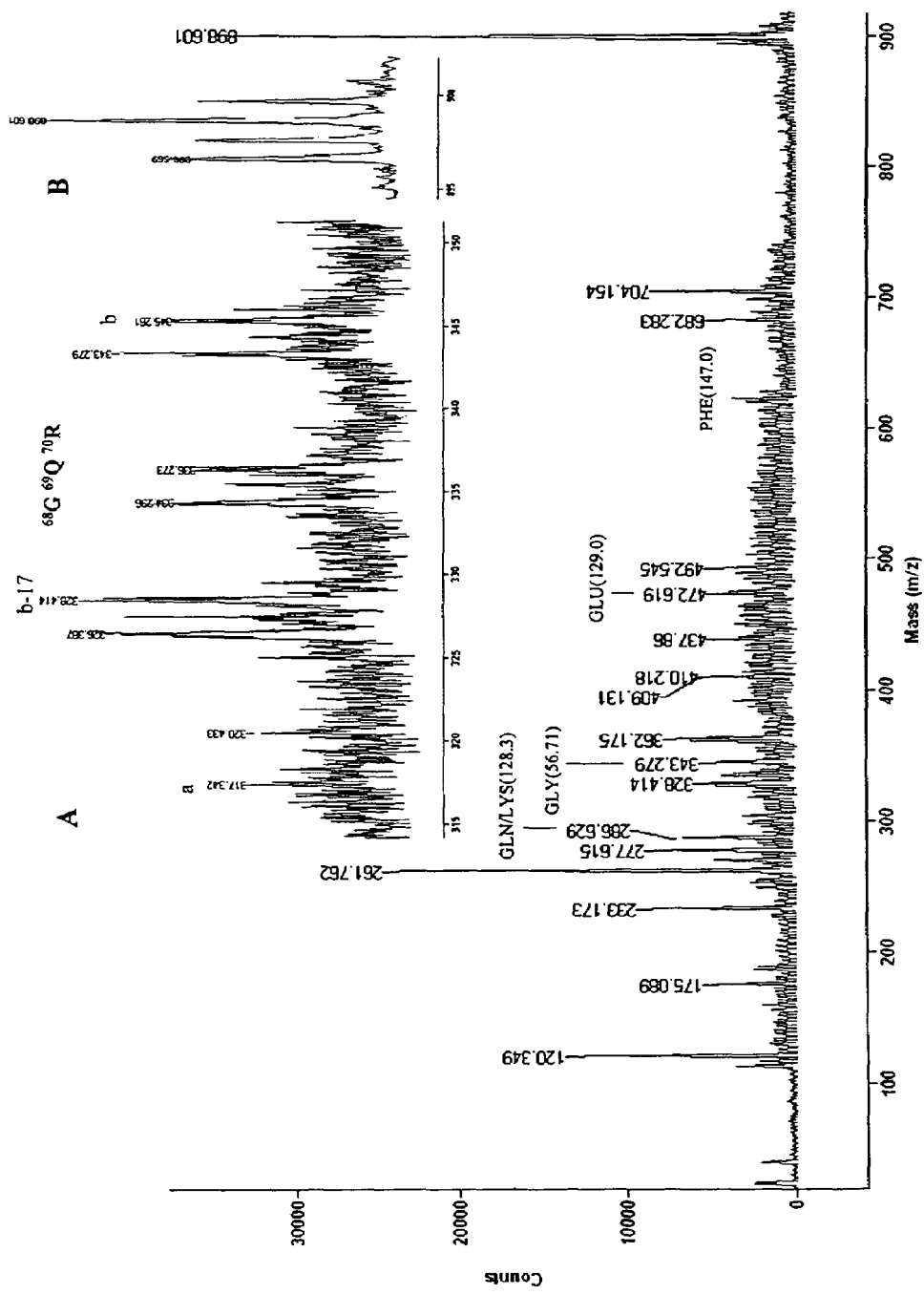
FIG. 3b shows postsource decay fragment ion mass spectra of the fragment of $^{64}$FLFEGQ$^{70}$R containing the labeled glycine residue, Gly-$d_2$.

As illustrated above, these stable isotope-labeled residues in proteolytic peptides are useful indicators of the amino acid composition of mass-tagged peptides. In addition, the characteristic mass-split pattern can further serve as internal markers in the PSD spectra to obtain detailed sequence information on mass-tagged peptides from a protein. FIG. 3a shows the PSD fragment ion mass spectrum of the fragment of $^{64}$FLFEGQ$^{70}$R containing unlabeled glycine residue. The insets show expanded views of the monoisotopic peaks of smaller PSD fragment ions in the m/z range of (A) 300–350 Da, and (B) the precursor ion, M$^+$=896.60. It is to be noted that there is no immediate information concerning residue assignment in the spectrum even using the PSD tool box in the software of the PE MALDI-TOF MS instrument. This is due to the complexity of the fragmentation pattern. Many low-intensity precursor ions produced by delayed-extraction MALDI do not yield enough PSD fragmentation to allow the derivation of even short sequence tags. To demonstrate the use of labeled amino acid precursors for rapid peptide sequencing, a peptide fragment containing 50% of the labeled residue, Gly-d$_2$, was selected for PSD experiments. FIG. 3b shows the PSD fragment ion mass spectra of the fragment of $^{64}$FLFEGQ$^{70}$R containing 50% labeled glycine residue, Gly-d$_2$. The insets show expanded views of the monoisotopic peaks of smaller PSD fragment ions in the m/z range of (A) 300–350 Da, and (B) the precursor ion, M$^+$=896.604. The M$^+$ ion of 50% Gly-d$_2$ at 896.67 Da (FIG. 3b, inset B) was selected as a PSD precursor because the characteristic mass-split pattern indicates the location of the labeled glycine residue in the progressively produced fragment ions through PSD. The gate width was adjusted for the full isotopic distribution pattern of the PSD fragments. For smaller PSD fragment ions in the m/z range of 300–370 Da, several peak sets with the characteristic mass-split pattern of the partially Gly-d2-labeled fragments were immediately observed (FIG. 3b, inset A). The a-17/a/b-17/b cursor available in the PSD tool box was applied to verify that the Gly containing b ion was at 343.27 Da. The determination of the b ion is a critical step for the residue assignment in peptide sequencing using PSD. This identified b ion was then used as an internal marker to trace the neighboring amino acid residues. $^{67}$Glu, and $^{69}$Gln have been identified as the closest amino acids to the Gly-d$_2$, and the peak of 343.27 Da was assigned to the fragment ion of $^{67}$EGQ. From this core residue of $^{68}$Gly-d$_2$, the sequence of the M$^+$ fragment of 896.67 Da has been determined.

Figure 4A:
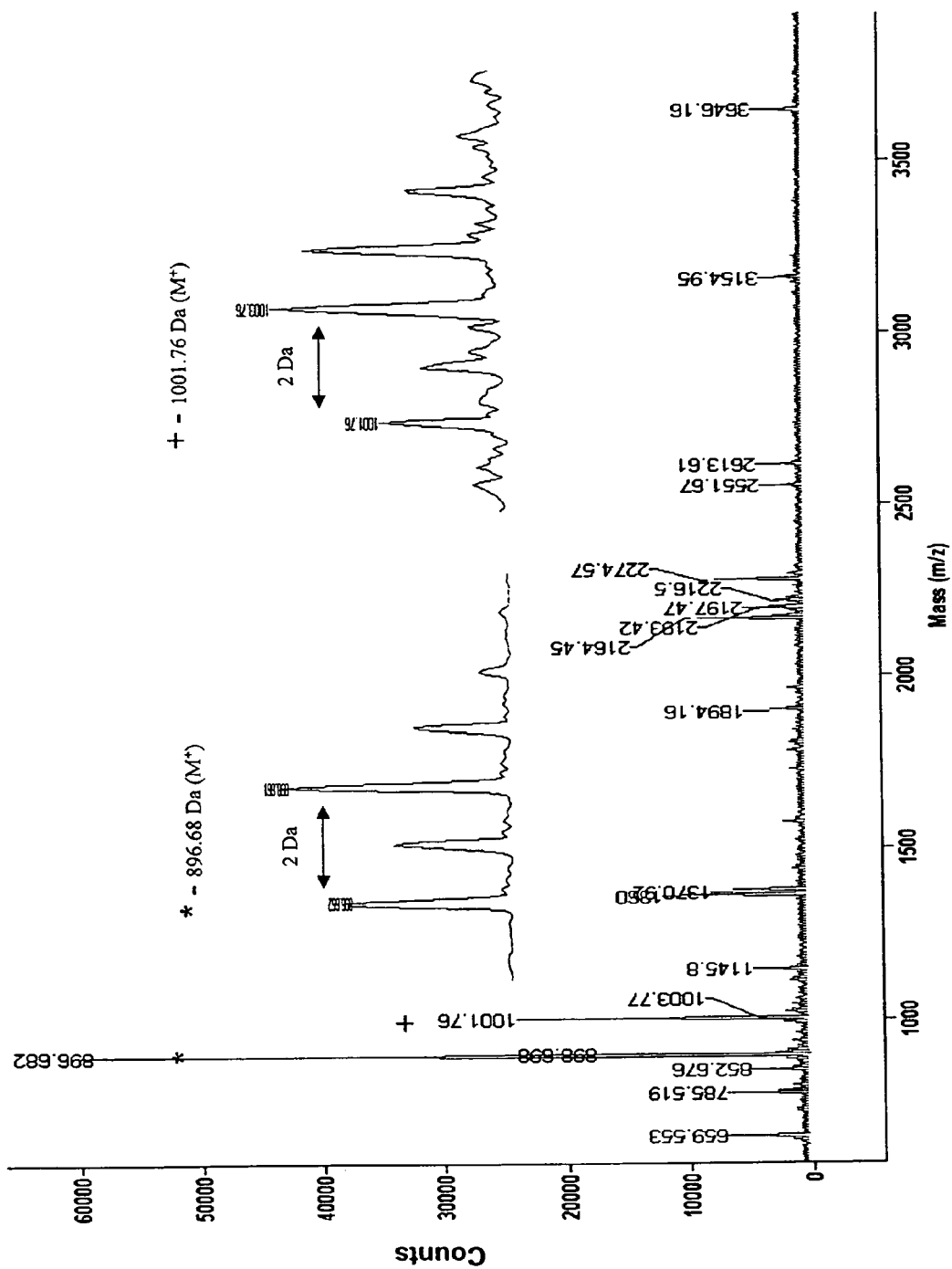
Figure 4B:
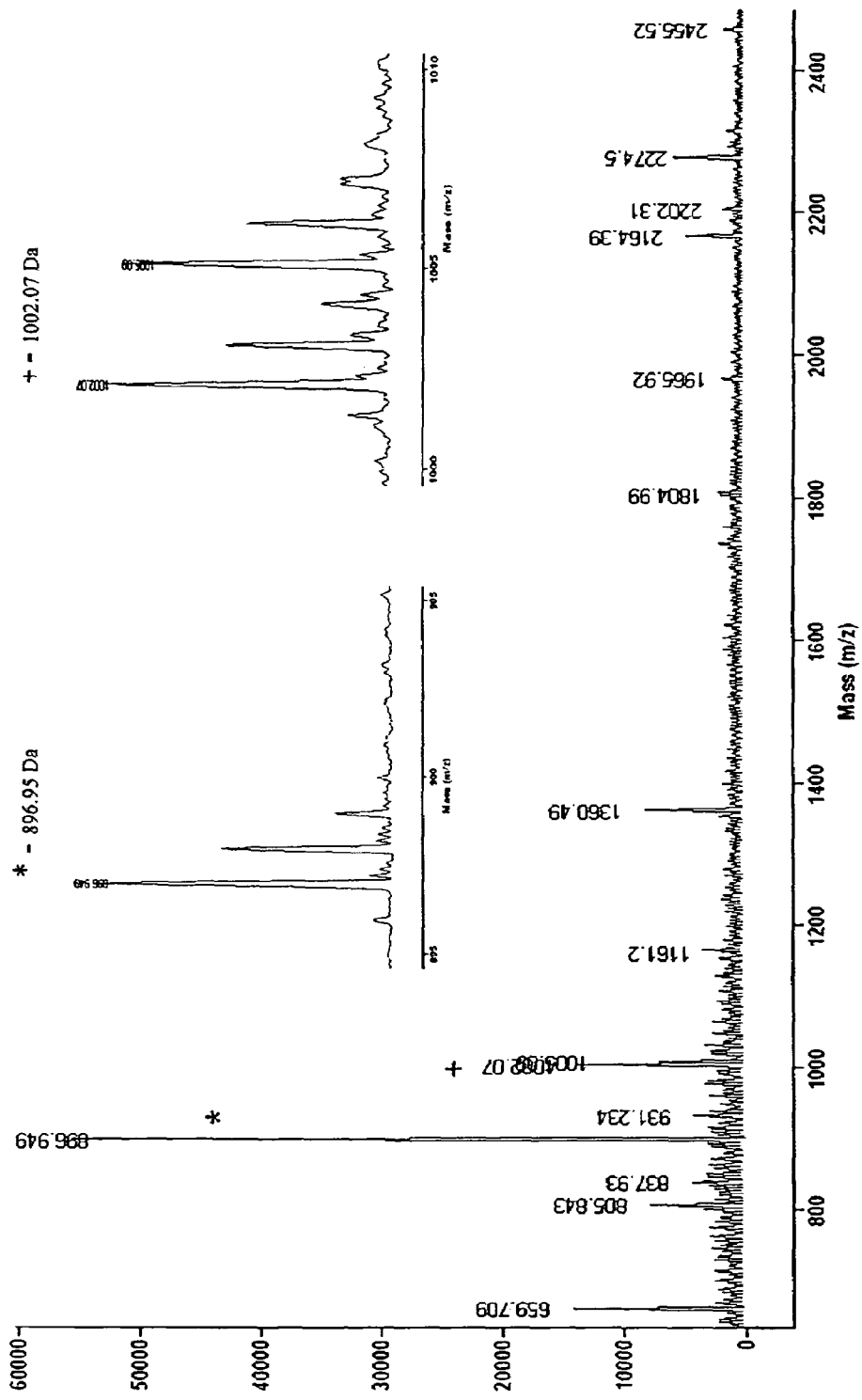
FIG. 4b shows delayed-extraction MALDI mass spectra of tryptic digests of 50% Met-$d_3$ labeled E. coli cell lysate.

C. Identification of UBL1 in an *E. coli* Cell Extract. The mass-tagged peptides of UBL1 in the proteolytic digests of a protein extract from *E. coli* were also identified. FIG. 4a shows the delayed-extraction MALDI mass spectra of tryptic digests of the cell lysates for the 50% Gly-d$_2$ labeled *E. coli* cell lysate, while FIG. 4b shows that for the 50% Met-d$_3$ labeled *E. coli* cell lysate. The peaks at 896.67 Da (M$^+$ion) and 1001.75 Da (M$^+$ ion) each with the characteristic 2 Da mass-split were clearly observed and result from Gly-d$_2$ labeling of UBL1 in the presence of tryptic peptides from the cellular proteins. A 3 Da mass-split was found for the peak of 1001.75 Da (M$^+$), but not for the peak of 896.67 Da (M$^+$) when 50% Met-d$_3$ was used as the labeling precursor. Thus, these two specific UBL1 peptides indicate the presence of UBL1 in the cell extract.

D. Identification of Individual Proteins in a Complex Mixture. It is known that the UBL1 interacts with the ubiquitin-conjugating enzyme (UBC9) during DNA double-strand break repair[33]. To demonstrate the use of the method of the present invention for unique protein identification in a complex mixture, both proteins in *E. coli* cells and identified mass-tagged peptides from each of these two proteins have been specifically labeled. These mass-tagged peptides characterized by their m/z values and partial amino acid composition are considered to be the fingerprints of these proteins.

Figure 5:
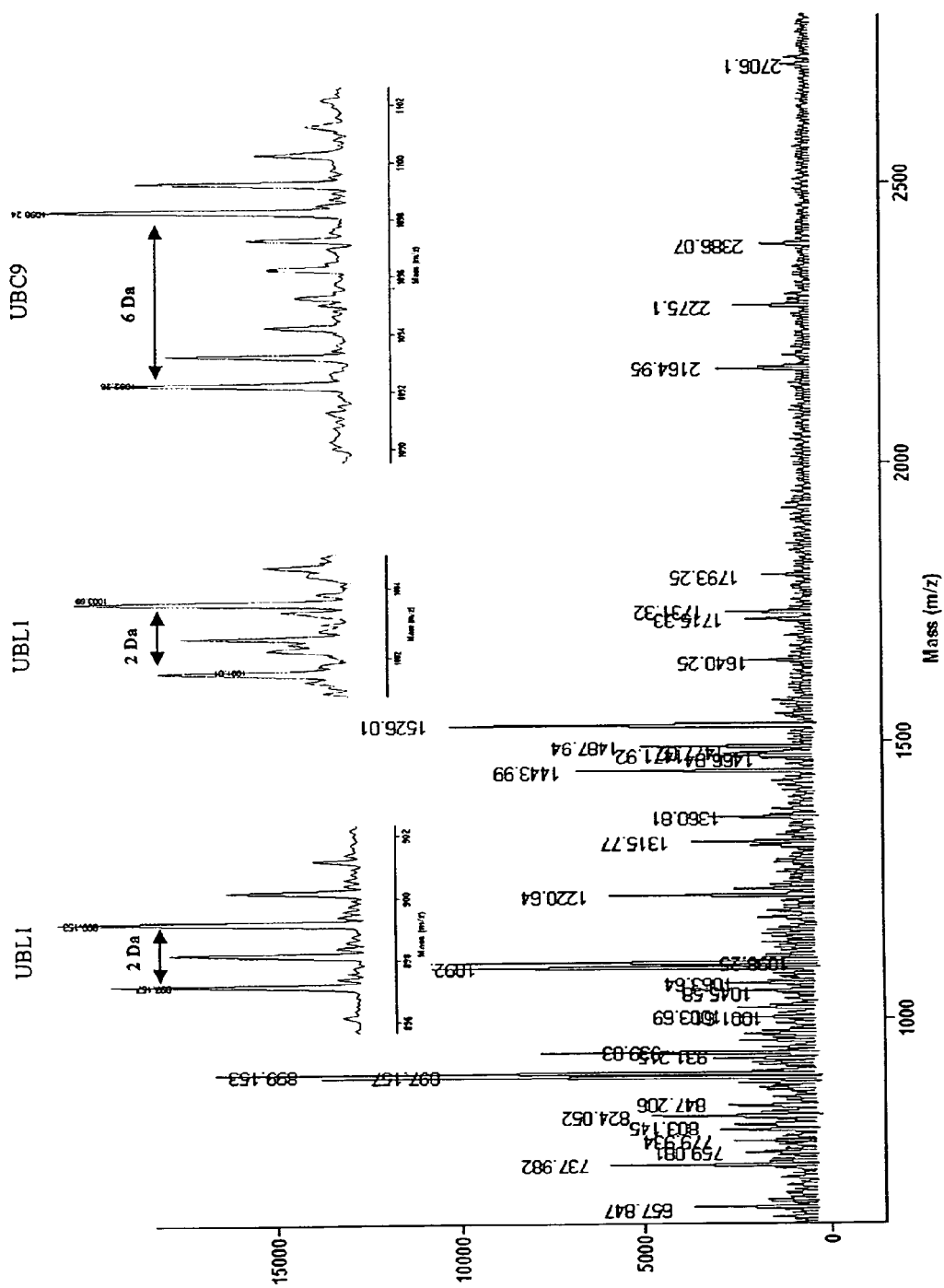
FIG. 5 shows the delayed-extraction MALDI-TOF spectrum of the tryptic digests of the complex of interacting proteins of UBL1 and UBC9.

FIG. 5 shows the MALDI-TOF spectrum of the tryptic digest of the complex which shows the peak pairs with 2×n Da mass-split ("n" represents the number of glycine residues) with about a 1:1 intensity ratio resulting from specific-labeled glycine-containing peptides. Three such characteristic peak pairs have been observed in the mass spectrum from the pool of tryptic digests. They are the peak pairs at 896.67 Da (M$^+$ ion) and 1001.75 Da (M$^+$ ion) each with the characteristic 2 Da mass-split, and a pair of M$^+$ ions at 1092.25 Da and 1098.31 Da with a 6 Da in spacing. The former two peak sets are mass-tagged peptides of UBL1 protein. The latter pair indicates that the fragment ion contains three glycines. The matched peptide is the GTP-WEGGLFK (the theoretical m/z value of the M$^+$ ion is 1091.55 Da) of UBC9 protein. To confirm the assignment, the ratio of unlabeled to labeled amino acid precursors was varied. The change of the relative intensity of 1092.25 Da (M$^+$ ion) to 1098.31 Da (M$^+$ ion) was in agreement with this assignment. Therefore, not only from their matched m/z values, but also from their amino acid compositions, the above assigned peptides provide "fingerprints" for the identifications of UBL1 and UBC9.

III. Discussion:

A. Mass-tag Measurements are Relative and More Accurate.

Mass calibration was performed externally using the calibration standard, Calmix 2 (PE Biosystem). Typical observed mass errors were ±0.2 to ±0.4 Da compared to the theoretically calculated masses for most peptides, which is expected for routine MALDI-TOF measurements. The use of absolute m/z values of measured peptides with such large errors (about 250 ppm) in database searching can result in the identification of a number of proteins other than the target protein. An advantage of the mass-tagging method of the present invention is that the mass of the tags requires only relative measurements; that is, the mass difference between the labeled and unlabeled peptides. For example, whereas the absolute m/z value of an ion peak is in error by 0.4 Da in the spectrum of FIG. 2a (A) (1001.75) when compared to FIG. 2a (B) (1002.15), the mass tag of 3 Da difference was accurately determined for a mixture of the labeled and unlabeled peptide (FIG. 2a (C)). Therefore, relative mass tag measurements reduce the demand for ultrahigh precision in the absolute m/z values of proteolytic fragments, which is currently required for protein database searching. More importantly, because mass tag measurements are relative, the identification of mass-tagged peptides will also be free of uncertainties from functional post-translation modifications and chemical modifications resulting from chemical reactions during polyacrylamide gel electrophoresis. The signals from mass-tagged peptides can be corroborated by changing the relative ratio of the labeled to unlabeled amino acid precursors.

B. Mass Tagging Provides Another Parameter for Unique Protein Identification.

After separation of a protein complex by 2D PAGE[3,5,6], individual spots often contain several proteins which complicates protein assignments from proteolytic digests. However, mass tagging with particular amino acids provides some amino acid composition data on the labeled peptides that can be used as an additional constraint for the m/z values used to identify these peptides. Experimentally, mass tagged peptides can easily be distinguished from a pool of peptides by their characteristic mass-splitting patterns. The magnitude of the mass tags that are correlated with the partial amino acid composition of peptides in data searches allows the identification of a target protein from only a few mass-tagged peptides in the digest pool. It is also noted in the TABLE that there are several tryptic fragments of UBL1 (that is, 730.39, 738.37, and 1750.78 Da) that are either too weak to be of use, or missing from the mass spectrum. These missing peptides however become less significant for protein identification as long as other mass-tagged peptides can be identified in a residue-specific manner.

C. Implications of the Site-specific Labeling Technique for Proteome Identification.

The present method is also generally applicable for the identification of unique proteins in a complex. Residue-specific labeling in *E. coli*-expressed proteins using genetically engineered *E. coli* cell strains has been demonstrated. We have also examined isotopic scrambling of the residue-specific labeling of the protein, UBL1, with proteins of the *E. coli* BL21(DE3) cell host. In the M9 media enriched with the 20 amino acids, the stable isotope enriched amino acids, L-Methionine-99.9%-d$_3$ (Met-d$_3$) and Glycine-99.9%-2,2-d$_2$ (Gly-d$_2$), were used as the mass-tagging precursors for the methionine and glycine sites respectively. Negligible scrambling of the labels to other types of residues was observed for the short growth period. By taking up amino acids directly from the Minimum Essential Media[34] supplemented with a high concentration of all 20 amino acids including labeled precursors, proteins expressed in mammalian cells can also be labeled with specific amino acid(s). Within an appropriate growing time, all proteins expressed in the media will be mass-tagged in those segments containing the labeled amino acids.

Residue-specific mass tagging is particularly useful for the direct analysis of large protein complexes, when a denatured and reduced protein complex is first digested to peptide fragments in a sequence-specific manner, followed by liquid chromatography separation and MS analysis[4]. The experimentally measured m/z values of mass-tagged peptides can be compared with the calculated m/z values of a proteolytic peptide library derived from the predicted digestion of proteins translated from the genomic sequence databases. The mass-tagged peptides identified from the matches will be selected for the search and identification of unique proteins present in the translated genomic databases. Because the mass tags in different proteins are sequence-specific and correlated with their amino acid composition, this process will help resolve the mass degeneracy arising from peptides with the same m/z values. In our data bank, both the m/z values of peptides and the mass tags of certain peptides can be utilized in selective database searches for the unique identification of different proteins in complex mixtures. The specificity and accuracy of protein identification will be significantly increased by this analytical methodology of residue-specific mass tagging.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

REFERENCES

1. W. P. Blackstock and M. P Weir, *Trends in Biotech.* 1999, 17, 121–127.
2. J. R. Yates, *J. of Mass Spectrom.* 1998, 33, 1–19.
3. G. Neubauer et al., *Nature Genetics* 1998, 20, 46–50.
4. A. Link et al., J. R. *Nature Biotech* 1999, 17, 676–682.
5. P. Chaurand et al., *J. of Am. Soc. for Mass Spectrom.* 1999, 10, 91–103.
6. A. Shevchenko et al., *Proc Natl. Acad. Sci. USA* 1996, 93, 14440–14445.
7. C. Scheler et al., *Electrophoresis* 1998, 19, 918–927.
8. M. Kussmann et al., *J. of Mass Spectrom.* 1997, 32, 593–601.
9. S. L. Cohen and B. T. Chait, *Anal. Chem.* 1996, 68, 31–37.
10. F. Amado et al., *Rapid Commun in Mass Spectrom.* 1997, 11, 1347–1352.
11. Y. F. Zhu et al., *Rapid Commun in Mass Spectrom.* 1995, 9, 1315–1320.
12. E. Krause et al., *Anal. Chem.* 1999, 71, 4160–4165.
13. Z. Olumee et al., *Rapid Commun in Mass Spectrom.* 1995, 9, 744–752.
14. H. Wenschuh et al., *Rapid Commun in Mass Spectrom.* 1998, 12, 115–119.
15. P. M. Rudd et al., *Biochemistry* 1994, 33, 17–22.
16. M. Wang and A. G. Marshall, *Anal. Chem.* 1989, 61, 1288–1293.
17. B. vandenBerg et al., *J. Mol. Biol.* 1999, 290, 781–796.
18. K. Rose et al., *Biochem. J.* 1983, 215, 273–277.
19. J. Qin et al., *Rapid Commun in Mass Spectrom.* 1998, 12, 209–216.
20. A. Ono et al., Stable Isotope Applications in Biomolecular Structure and Mechanisms (Ed. J. Trewhella et al.) (Los Alamos Natl. Lab., New Mexico).
21. Y. Oda et al., *Proc Natl. Acad. Sci. USA* 1999, 96, 6591–6596.
22. P. K. Jensen et al., *Anal. Chem.* 1999, 71, 2076–2084.
23. X. Chen et al., *Anal. Chem.* 1999, 71, 3118–3125.
24. D. S. Waugh, *J. Biomol. NMR* 1996, 8, 184–92.
25. D. C. Muchmore et al., *Methods in Enzymology* 1989, 177, 45–71.
26. T. Yabuki et al., *J. Biomol NMR* 1998, 11, 295–306.
27. F. Hillenkamp et al., *Anal. Chem.* 1991, 63, 1193A–1203A.
28. O. N. Jensen et al., *Rapid Commun in Mass Spectrom.* 1996, 10, 1371–1378.
29. R. Kaufmann et al., *Rapid Commun in Mass Spectrom.* 1996 10, 1199–1208.
30. T. Keough et al., *Proc. Natl. Acad. Sci. USA* 1999, 96, 7131–7136.
31. Z. Shen et al., *Genomics,* 1996, 37, 183–186.
32. P. Bayer et al., *J. Mol. Biol.* 1998, 280, 275–286.
33. Q. Liu et al., *J. Biol. Chem.* 1999, 274, 16979–16987.
34. Gibco BRL products & reference guide 2000–2001 pp 1-1–10-1.

TABLE

Theoretical Masses and Sequences of Proteolytic Fragments (>500 Da) from Trypsin Digested UBL1

| Fragment# | Sequential# | Monoisotopic [M+] | Sequence |
|---|---|---|---|
| 3* | 18–23 | 738.37 | EGEYIK |
| 7* | 40–45 | 730.39 | MTTHLK |
| 10 | 49–54 | 785.33 | ESYCQR |
| 12 | 64–70 | 896.46 | FLFEGQR |
|  |  | 898.46 | FLFEG($d_2$)QR |
| 13 | 71–78 | 895.46 | IADNHTPK |
| 11 | 55–63 | 1001.52 | QGVPMINSLR |
|  |  | 1003.52 | QG($d_2$)VPMNSLR |
|  |  | 1004.52 | QGVPM($d_3$)NSLR |
| 5 | 26–37 | 1359.69 | VIGQDSSEIHFK |
| 1* | 1–16 | 1750.78 | MSDQEAKPSTEDLGDK |
| 14 | 79–107 | 3643.63 | ELGMEEEDVIEVYQEQT-GGHSTVLEHHHHHH |
|  |  | 3649.63 | ELG($d_2$)MEEEDVIEVYQEQT-G($d_2$)G($d_2$)HSTVLEHHHHHH |
|  |  | 3646.63 | ELGM($d_3$)EEEDVIEVYQEQT-GGHSTVLEHHHHHH |

*weak or missing peaks in MS peptide map.
Amino acid sequence of UBLI: MSDQEAKPST EDLGDKKEGE YIKLKVIGQD SSEIHFKVKM TTHLKKLKES YCQRQGVPMN SLR FLFEGQR IADNHTPKELGMEEEDVIEVYQEQTGGHSTVLEHHHHHH

What is claimed is:

1. A method for identifying a protein, the method comprising the steps of:
    (a) separating the protein from other proteins;
    (b) digesting the protein, thereby forming first proteolytic peptides;
    (c) acquiring a monoisotopic mass distribution spectrum of the first proteolytic peptides and acquiring the m/z values for the first proteolytic peptides;
    (d) introducing at least one amino acid 100% labeled with at least one stable isotope into a cell that expresses a protein, and wherein the cell is induced to express the protein comprising the at least one amino acid 100% labeled in a sequence-specific manner;
    (e) separating the protein bearing the at least one labeled amino acid from other proteins;

(f) digesting the protein bearing the at least one labeled amino acid, thereby forming second proteolytic peptides;

(g) acquiring the monoisotopic mass distribution spectrum of the second proteolytic peptides and acquiring the m/z values for the first proteolytic peptides;

(h) comparing the monoisotopic mass distribution spectrum of the second proteolytic peptides with the monoisotopic mass distribution spectrum of the first proteolytic peptides to determine the amino acid composition of the first proteolytic peptides and the second proteolytic peptides, whereby the protein is identified from the m/z values of the first proteolytic peptides and the m/z values of the second proteolytic peptides and the amino acid composition of the first proteolytic peptides and the second proteolytic peptides.

2. The method as described in claim 1, wherein the cell is selected from a strain of cells containing genetic lesions for controlling amino acid biosynthesis such that endogenous amino acid biosynthesis and scrambling of the label to other types of residues are avoided.

3. The method as described in claim 2, wherein the strain of cells comprises *Escherichia coli*.

4. The method as described in claim 1, wherein said step of inducing the cell to express the protein is achieved using isopropylthiogalactoside.

5. The method as described in claim 1, wherein the at least one 100% labeled amino acid is selected from the group consisting of L-Methionine-$d_3$ and Glycine-2,2-$d_2$.

6. The method as described in claim 1, wherein said step of digesting the protein, forming first proteolytic peptides and said step of digesting the protein bearing the at least one labeled amino acid, and forming second proteolytic peptides are achieved using a protease.

7. The method as described in claim 6, wherein said protease comprises trypsin.

8. The method as described in claim 1, wherein said step of separating the protein and said step of separating the protein bearing the at least one labeled amino acid comprise the use of 2-D gels.

9. The method as described in claim 1, wherein said steps of separating the protein and said step of separating the protein bearing the at least one labeled amino acid comprise the use of liquid chromatography.

10. The method as described in claim 1, wherein said steps of obtaining the monoisotopic mass distribution spectrum of the first proteolytic peptides and acquiring the m/z values, and obtaining the monoisotopic mass distribution spectrum of the second proteolytic peptides and acquiring the m/z values are achieved using a mass spectrometer selected from the group consisting of matrix-assisted laser desorption/ionization time-of-flight mass spectrometers and electrospray mass spectrometers.

11. The method as described in claim 10, wherein post-source decay fragment ion spectra are acquired.

12. The method as described in claim 10, wherein delayed-extraction mass spectra are acquired.

13. The method as described in claim 1, wherein the at least one 100% labeled amino acid is diluted with a variable amount of an unlabeled form of the same amino acid before said step of introducing the amino acid into a cell that expresses the protein, whereby the amino acid composition of each first peptide is confirmed.

14. The method as described in claim 1, wherein the at least one stable isotope is selected from the group consisting of $^{13}C$, $^{15}N$ and $^2H$.

15. The method as described in claim 1, wherein the monoisotopic mass distribution spectrum of a sufficient number of first proteolytic peptides and the m/z values are acquired, and wherein the monoisotopic mass distribution spectrum of a sufficient number of second proteolytic peptides and the m/z values are acquired such that a proteome is identified.

16. A method for identifying a protein which comprises the steps of:

(a) incorporating at least one amino acid 100% labeled with at least one stable isotope into the protein in a sequence-specific manner at a variable number of the sites for the at least one amino acid in the protein, forming thereby a mixture of partially labeled proteins;

(b) introducing the at least one 100% labeled amino acid and a selected amount of an unlabeled same at least one amino acid into a cell that expresses the protein, wherein the cell is selected from a strain of cells containing genetic lesions for controlling amino acid biosynthesis such that endogenous amino acid biosynthesis and scrambling of the label to other types of residues are avoided;

(c) inducing the cell to express the protein comprising the at least one 100% labeled amino acid or the unlabeled at least one amino acid in a sequence-specific manner;

(d) separating the mixture of partially labeled proteins from other proteins;

(e) digesting the mixture of partially labeled proteins, thereby forming proteolytic peptides; and (f) acquiring the monoisotopic mass distribution spectrum of the proteolytic peptides and acquiring the m/z values therefor, whereby the protein is identified from the m/z values of the proteolytic peptides and the amino acid composition of the proteolytic peptides.

17. The method as described in claim 16, wherein the strain of cells comprises *Escherichia coli*.

18. The method as described in claim 16, wherein said step of inducing the cell to express the protein is achieved using isopropylthoigalactoside.

19. The method as described in claim 16, wherein the at least one 100% labeled amino acid is selected from the group consisting of L-Methionine-$d_3$ and Glycine-2,2-$d_2$.

20. The method as described in claim 16, wherein the selected amount of unlabeled at least one amino acid is 50%.

21. The method as described in claim 16, wherein said step of digesting the protein forming peptides is achieved using a protease.

22. The method as described in claim 21, wherein said protease comprises trypsin.

23. The method as described in claim 16, wherein said step of separating the mixture of partially labeled proteins comprises using 2-D gels.

24. The method as described in claim 16, wherein said steps of separating the mixture of partially labeled proteins comprises using liquid chromatography.

25. The method as described in claim 16, wherein said step of obtaining the monoisotopic mass distribution spectrum of the peptides and acquiring the m/z values therefor is accomplished using a mass spectrometer selected from the group consisting of matrix-assisted laser desorption/ionization time-of-flight mass spectrometers and electrospray mass spectrometers.

26. The method as described in claim 25, wherein post-source decay fragment ion spectra are acquired.

27. The method as described in claim 25, wherein delayed-extraction mass spectra are acquired.

28. The method as described in claim 16, wherein the amount of the unlabeled form of the at least one amino acid is varied such that the amino acid composition of each peptide is confirmed.

29. The method as described in claim 16, wherein the at least one stable isotope is selected from the group consisting of $^{13}C$, $^{15}N$ and $^{2}H$.

30. The method as described in claim 16, wherein the monoisotopic mass distribution spectrum of a sufficient number of proteolytic peptides and the m/z values are acquired such that a proteome is identified.

* * * * *